(12) United States Patent
Borden et al.

(10) Patent No.: US 6,338,944 B1
(45) Date of Patent: Jan. 15, 2002

(54) METHODS FOR MEASURING STROMELYSIN-1 PROMOTER ACTIVITY

(75) Inventors: Paula Ann Borden, Palo Alto; Renu Anand Heller, Stanford, both of CA (US)

(73) Assignee: Syntex (U.S.A.) Inc., Palo Alto, CA (US)

( * ) Notice: Subject to any disclaimer, the term of this patent is extended or adjusted under 35 U.S.C. 154(b) by 0 days.

(21) Appl. No.: 09/549,808

(22) Filed: Apr. 14, 2000

Related U.S. Application Data

(62) Division of application No. 09/174,756, filed on Oct. 19, 1998, now abandoned, which is a division of application No. 08/362,706, filed on Dec. 23, 1994, now Pat. No. 5,824,794.

(51) Int. Cl.[7] .......................... C12Q 1/68; C12N 15/00; C12N 5/00; C12N 5/08; C07H 21/04

(52) U.S. Cl. ..................... 435/6; 435/320.1; 435/325; 435/366; 536/23.1; 536/23.4; 536/24.1

(58) Field of Search .............................. 536/24.1, 23.1, 536/23.4; 435/320.1, 325, 366, 6

(56) References Cited

PUBLICATIONS

Quinones, et al., "Transcriptional Regulation of Human Stromelysin", (1989) *J. Bio. Chem.* 264: 8339–8344.

Buttice, et al., "The AP–1 site is required for basal expression but is not necessary for TPA–response of the human stromelysin gene", (1991) *Nucleic Acids Res.* 19:3723–3731.

Frisch and Ruley, "Transcription from the Stromelysin Promoter Is Induced by Interleukin–1 and Repressed by Dexamethasone", (1987) *J. Bio. Chem.* 262:16300–16304.

Buttice and Kurkinen, "A Polyomavirus Enhancer A–binding Protein–3 Site and Ets–2 Protein Have a Major Role in the 12–0–Tetradecanoylphorbol–13–acetate Response of the Human Stromelysin Gene", (1993) *J. Biol. Chem.* 268:7196–7204.

Birkedal–Hansen, et al., "Matrix Metalloproteinases: A Review", (1993) *Crit. Revs. in Oral Biol. & Med.* 4(2):197–250.

Sirum–Connolly and Brinckerhoff, "Interleukin–1 or phorbol induction of the stromelysin promoter requires an element that cooperates with AP–1", (1991) *Nucleic Acids Res.* 19:335–341.

Sirum and Brinckerhoff, "Cloning of the Genes for Human Stromelysin and Stromelysin 2: Differential Expression in Rheumatoid Synovial Fibroblasts", (1989) *Biochem.* 28:8691–8698.

Diaz–Meco, et al., "Protein Kinase C–independent Expression of Stromelysin by Platelet–derived Growth Factor, ras Oncogene, and Phosphatidylcholine–hydrolyzing Phospholipase C" (1991) *J. Biol. Chem.* 266:22597–22602.

Matrisian, et al., "Isolation of the Oncogene and Epidermal Growth Factor–Induced Transin Gene: Complex Control in Rat Fibroblasts", (1986) *Mol. & Cell. Bio.* 6:1679–1686.

*Primary Examiner*—Ardin H. Marschel
*Assistant Examiner*—Shubo Joe Zhou
(74) *Attorney, Agent, or Firm*—Heller Ehrman White & McAuliffe LLP

(57) ABSTRACT

This invention relates to a human stromelysin-1 (i.e., HSL-1) promoter and uses therefor. In particular, the invention provides a purified DNA containing a functional HSL-1 promoter region that corresponds in structure to the native genomic form of this promoter, an expression vector containing a portion of the purified promoter DNA operatively linked to a heterologous DNA sequence encoding a detectable gene product, a host cell transformed with this factor, a pharmacologic screening assay for stromelysin-1 promoter modulating activity, and a method of modulating TNF α level and matrix metalloproteinase activities in inflamed tissues of a mammal.

2 Claims, 12 Drawing Sheets

1.7-kb strom promoter Sequence

```
         10         20         30         40         50         60         70         80         90        100        110        120        130        140        150
1234567890 1234567890 1234567890 1234567890 1234567890 1234567890 1234567890 1234567890 1234567890 1234567890 1234567890 1234567890 1234567890 1234567890 1234567890

MscI
                                                              BalI
EcoRI                                              BaeI  SspI                                                         XamI                         SpeI    DraI
GAATTCACAT CACTGCCACC ACCTCTTCT CCTTGTCCTC ATATCAATGT GGCCAAATAT TTTCCCTGTA TTTCAATCAG GACAAGACAT GGTTTTTTCC CCCCATCAAA GGAATGGAGA ACCATAGAAT ACTAGTGTTA AAATGTCTTT -1557
                                                                          SacI
                                                                          HgiAI
                                                                          Bsp1286I
       NlaIV                                                              BanII              Ecl136II   SecI                                                DraI
       BanI                                                                                                                                                           
AGGCCAGGTG CCCTGACCA TGTCTGTAAT CCTAGCACTT TGAGAGGTTG ATCATTGAT ATCACTTGAT CCCAGAGCTC GAAACCAGCC TGGGCAACAT CTGTCCCTAT TTTTTAAATA AACTTGAAA AGTCTTTAG -1407

BstYI               DraI
ACATAATTCA GTCTATAAAT GAAGGCTTAA ATGTGATGTA TAGCCCCCTG CCAAGTGGCT ATACCCTGTG TGGGCATCTT CAGTCATAGG GATCTTATTG CCACAGAGAA ATCCCTTCCA ACTTATTGGG TAAAATCTCT CCAAGTTTA -1257

Bsp1286I                                                                                                     DraI
TTAAGAAACA CACAAAAAAT AAAGCAAGA AGAAAATGCA AAAGTTAT AAATGAGAGG GGGACTTATT AAA GGTCTAA TAAAATGCACA TTTGTATCCA TCATTCTACT GAGTTCTTAC TCCCAAGATG TTCTTCCCTT -1107
```

FIG. 3A 1.7-kb strom promoter Sequence

```
         10         20         30         40         50         60         70         80         90        100        110        120        130        140        150
1234567890 1234567890 1234567890 1234567890 1234567890 1234567890 1234567890 1234567890 1234567890 1234567890 1234567890 1234567890 1234567890 1234567890 1234567890
                                                                       BclI              BspMI                              BbsI                          BsmI
                                                                       ▶                 ▶                                 ▶                              ▶
TAGCAAACAA ATAACCAAGT CAGCAAAGAA AGAAAGAACA AACAAAAATGT GGTGATCAGG GAACCATTGA GGAGATGGAT GGTGCCAGGT GCCAAGAGGA CTATAAAGT TTTACAAAAT GTCTTCCTCT GAATATGTTT AGAGTCTTGC -957

EarI    EarI
                                                                                                  ▶       ▶
ATTCAAGCAT TTATTATACA ACCAATAATG TGAGCCAACAC TTTACTTGAC AAAGAAACAG AACAGAAGAG CATGAAGACA AAATTTAGGA TGGATTCTGT TCTTCAACTT CAAAGCATCT GCTAATTTGA -807
                                                                                                                                          Bsp1286I
                                                                                                                                          BanII
                                                                                                                                          ApaI       XamI
                              NspHI                                                                                                       BsaAI NlaIV AseI
                              AflIII      BbsI                                                                                            ▶           ▶
ATTTAGGGAG GAGGGGAAAA GGTTGAAAGA GAATAAGACA TGTGTAGAAG ACAAGGACAG AGAGAATTTC AGTCCGGTAA GCAATGTAAT TCATTTCAGT TCTACAACTA TTTATGGAGC AGCTACGTGG GCCCATCACC CATTAATAAA -657

TTGGTTACAG AATTAAAAAC AACCCAAAGG GAATATACTT CCTTCTTTT CACAGACCCT CTTTGTCA TTCTCCCAT GAGGTTTTCC TCCTCAAGAA CCAGCAAATC CAACAGCAGT CAATAGCAGG CATTACAAAT CAGATTCAGA -507
```

FIG. 3B 1.7-kb strom promoter Sequence

```
         10         20         30         40         50         60         70         80         90        100        110        120        130        140        150
1234567890 1234567890 1234567890 1234567890 1234567890 1234567890 1234567890 1234567890 1234567890 1234567890 1234567890 1234567890 1234567890 1234567890 1234567890
                              ▶XbaI                                      ▶SfcI
GAAATAAATC ACCCCTTCTA AATTCTTTCT AGATATTATC TTTTATGTTT TGAGTATAAT TGTATATAGT ATAGACTATA GCTATGTATG TACACTTTCC ACTTACATCT TTTATTTGCT TTTATAATGT CTTTCTTAAA ATAAAACTGC  -357
                                                 ▶HincII                                                ▶EcoRI                                                   ▶XmnI
TTTTAGAAGT TCTGCACAAT TCTGATTTTT ACCAAGTCAA CCTACTTCTT CTCTCAAAAG GACAAACATA AATTGCTAG TGAATTCCAG TCAATTTTTC CAGAAGAAAA AAAATGCTCC AGTTTCTTCC TCTACCAAGA CAGGAAGCAC  -207
      ▶AseI                             ▶Dra  ▶AvaI
                                        ▶SecI
TTCCTGGAGA TTAATCACTG TGTTGCCTTG CAAATTGGG AAGCTGCGC TCCCGAGGTT GGACTTACAA GGAGGCAGGC AAGACGCAA GGCATAGAGA CAACATAGAG CTAAGTAAAG CCAGTGGAAA TCAAGCTGCG  -57

GGTGATCCAA ACAAACACTG TCACTCTTTA AAAGCTGCGC TCCCGAGGTT GGACTTACAA GGAGGCAGGC AAGACGCAA GGCATAGAGA CAACATAGAG CTAAGTAAAG CCAGTGGAAA TG   66
```

FIG. 3C

METHODS FOR MEASURING STROMELYSIN-1 PROMOTER ACTIVITY

This application is a division of application Ser. No. 09/174,756, filed Oct. 19, 1998, now abandoned, which is a division of application Ser. No. 08/362,706, filed Dec. 23, 1994, now U.S. Pat. No. 5,824,794, the disclosure of which is incorporated by reference herein.

FIELD OF THE INVENTION

This invention relates to a human stromelysin-1 (i.e., HSL-1) promoter and uses therefor. In particular, the invention relates to a purified DNA containing a functional HSL-1 promoter region that corresponds in structure to the native genomic form of this promoter, to an expression vector containing a portion of the purified promoter DNA operatively linked to a heterologous DNA sequence encoding a detectable gene product, and to the use of a host cell carrying the expression vector for drug screening and other pharmaceutical applications.

BACKGROUND

The stromelysin-1 promoter regulates the expression of the human stromelysin-1 gene, which encode major matrix metalloproteinase (MMP) of connective tissues. Stromelysin-2 and stromelysin-3 encoded by different genes and will not be discussed further here.

Stromelysin-1 degrades a broad spectrum of extracellular matrixother pharmaceutical applications. Components present in interstitial connective tissues, basement membranes, linings of the joints, and cartilage (e.g., proteoglycans, laminin, collagen IV, and fibronectin). It is currently reported that stromelysin indirectly stimulates the degradation of fibrillar collagens via proteolytic activation of procollagenases.

The controlled expression of stromelysin-1 is essential for tissue remodeling during normal development, wound healing, growth, aging and cellular responses to inflammation. Excessive matrix degradation contributes to the pathogenesis of a variety of disease-states, including rheumatoid- and osteoarthritis, bone resorption disease, abnormal angiogenesis, tumor invasion and metastasis, corneal ulceration and complications of diabetes. Thus an understanding of the regulation of stromelysin-1 promoter function has important consequences for the therapy of human diseases which involve increased expression of MMPs.

Aspects of stromelysin-1 promoter function have been studied using a portion of a 1.3 kb sequence isolated by Quinones et al from a circa 10 kb sequence upstream of the 5' transcription start site in a genomic clone of stromelysin-1 (Quinones et al, J. Biol. Chem. 264: 8339–8344 (1989); Buttice et al, Nucl. Acids Res. 19: 3723–3731 (1991); Diaz-Meco et al (J.Biol.Chem. 266: 22597–22602 (1991)), and a 0.30 kb sequence of a promoter region in a genomic clone isolated by Sirum and Brinkerhoff (Sirum and Brinckerhoff, Biochemistry 28: 8691–8698 (1989)).

The aforementioned 1.3 kb sequence extends 5' from the first ATG codon through the transcription start site to an Sst I site 1.3 kb upstream (−1303 to +66). A portion of this sequence (−1303 to −11) was cloned into a human growth hormone reporter gene vector, sequenced and studied. In transient transfection assays, it was determined that the 1.3 kb fragment contains DNA elements required for IL-1β induction and dexamethasone suppression, and that the level of induced expression varies inversely with fragment length. (Quinones et al, 1989). Responsiveness to PDGF and PC-PLC induction was localized to the region between −1279 and −1240. Diaz-Meco et al, J.Biol.Chem. 266: 22597–22602 (1991). Buttice et al cloned the portion −1303 to +4 into a human growth hormone reporter gene vector (henceforth referred to as −1303+4HGH) and demonstrated by transient transfection assays in mouse F9, HFF, HeLa and HepG2 cells that the AP-1 site (−70 to −64) was required for basal—but not for TPA-induced reporter gene expression. Buttice et al, Nucl. Acids Res. 19: 3723–3731 (1991).

Sirum and Brinckerhoff isolated human stromelysin-1 genomic clones and showed that the cloned DNA and human lymphocyte genomic DNA yielded the same-sized restriction fragments when digested with the restriction enzyme EcoRI (i.e. fragments of 1.4, 2.6 and 6 kb were detected by hybridization to a stromelysin cDNA probe). An EcoRI-DdeI promoter fragment from −325 to −18 relative to the AGT translation start codon was cloned into a CAT reporter gene vector. The vector was subsequently used to demonstrate that elements required for PMA, EGF and IL-1β induction were contained in about 270 bp of 5' flanking DNA.

Reporter gene constructs incorporating the above promoter fragments have provided confirmation that basal expression of stromelysin-1 is low in normal tissues, but can increase markedly in the presence of known inducers. H.Birkedal-Hansen et al, Critical Reviews in Oral Biology and Medicine, 4: 197–250 (1993); Buttice, G. and Kurkinen, M., J. Biol. Chem. 268: 7196–7204 (1992); Diaz-Meco, M. T. et al, J. Biol. Chem. 266: 22597–22602 (1991); Sirum-Connolly, K. and Brinckerhoff, C. E., Nucleic Acids Res. 19: 335–341 (1991). As well, the induction of stromelysin-1 gene expression can be inhibited by agents such as transforming growth factor-β, dexamethasone, retinoic acid, and cAMP. Birkedal-Hansen et al, (1993); Frisch, S. M. and Ruley, H. E., J. Biol. Chem. 262: 16300–16304 (1987).

Regulatory sequences that have been identified thus far appear to be highly conserved between species (see Matrisian et al, Mol. Cell Biol. 6: 1679–1686 (1986)(rat transin/stromelysin-1); Frisch and Ruley, J. Biol. Chem. 262: 16300–16304 (1987)), particularly in the region between −480 and transcription start site. However, as the present invention discloses, the region upstream of −480 contains a novel 1 kb sequence which is present in the genomic promoter in its native state but is absent from the 1.3 kb promoter region disclosed in Quinones et al (1989). PCR analysis and EcoRI restriction mapping both confirm the presence of this novel sequence. Also disclosed is the reappearance of the sequence of the published clone upstream of the 1 kb sequence, but in an inverse orientation.

Thus in addition to the functional regulatory sequences defined previously, the present invention possesses a native promoter architecture. The three dimensional relationship between enhancers and promoters is likely to be important for tissue- and developmental stage-specific transcription of MMP genes. For example, it is known that stromelysin-1 is coordinately expressed with other MMP genes in a cell type-specific manner. Birkedal-Hansen et al, (1993); Buttice et al (1991).

Given that the stromelysin-1 promoter is relatively quiescent in normal adult tissues but is activated under conditions of excessive extracellular matrix degradation (e.g., in inflammatory conditions, in some metastasizing tumors, and in rheumatoid arthritis and other diseases characterized by increased expression of metalloproteinases), the present invention is useful in ameliorating these conditions using gene therapy techniques, and in screening for pharmacologic agents that act transcriptionally to modulate stromelysin-1 levels.

SUMMARY OF THE INVENTION

An aspect of the present invention is to provide an isolated human stromelysin-1 promoter having a native genomic DNA promoter sequence of at least 1.7 kb upstream of the transcription start site.

Another aspect of the present invention is to provide a recombinant DNA molecule identified by SEQ ID NO:1, its complementary strand, high stringency-hybridizable nucleotide sequences thereof, and functional segments of the foregoing DNA sequences at least 1.47 kb in length.

Yet another aspect of the present invention is to provide the recombinant DNA sequence identified by SEQ ID NO:1, or a functional portion thereof, in a transfer vector for use in transferring the sequence to a host cell.

Another aspect of the present invention is to provide recombinant expression systems in which the DNA sequence (SEQ ID NO:1), or a functional portion thereof, is operably linked to a heterologous gene encoding a detectable product, preferably a reporter gene such as luciferase or β-galactosidase, most preferably the tumor necrosis factor-α receptor, TNFαR, or the tissue inhibitor of matrix metalloproteinases, TIMP. Still another object of the present invention is to provide such an expression system in a eukaryotic host cell that can be induced by inflammatory mediators (e.g., TNFα, IL-1β) and phorbol-type tumor promoters to express the product of the heterologous gene contained inserted into the vector. Yet another object of the invention is to provide a method of modulating extracellular levels of TNF-α and MMP activity by using the recombinant expression system to produce biologically active TNF-αR and TIMP.

Another aspect of the invention is to provide a recombinant expression system comprising at least 1.47 kb of the cloned promoter of the present invention operably linked to a reporter gene and contained within an appropriate host cell that can be used to assay for stromelysin-1 promoter activity, and a method for using this assay to screen for pharmacologic activators and inhibitors of stromelysin-1 promoter activity.

It should be understood that the foregoing general description and the following detailed description are intended to be exemplary and explanatory only, and not restrictive of the invention, as claimed.

BRIEF DESCRIPTION OF THE FIGURES

FIG. 1A shows the restriction map of the published stromelysin promoter, showing the locations of primers used for analysis. Arrows above the primers indicate the direction of priming. FIG. 1B shows the results of Southern blot analysis of PCR products generated by primer pairs A+B, C+D or A+D, using the indicated cloned stromelysin promoters as templates. The probe was a radiolabeled HindIII-BamHI fragment containing −1303 to +4 of the published human stromelysin promoter clone. PCR product sizes are indicated on the right. FIG. 1C shows Southern blots of human DNA samples subjected to PCR analysis using the same primer sets as in panel B. Two different exposure times are shown to facilitate visualization of the product of C+D.

FIG. 2B shows the presence of bands of 1.4, 2.6 and 6 kb in EcoRI-digested human DNA from four individuals.

FIGS. 3A–3C illustrates the nucleotide sequence of the stromelysin promoter region in pSKStrB from −1706 to the translation start codon (corresponding to SEQ ID NO:1). The positions of the named restriction enzyme sites are shown by arrowheads positioned above the sequence.

FIG. 7A shows a lacZ reporter gene vector map. FIG. 7B shows the luciferase reporter gene vector pGL-Basic map.

DETAILED DESCRIPTION OF THE INVENTION

Definitions

Figure 1A:
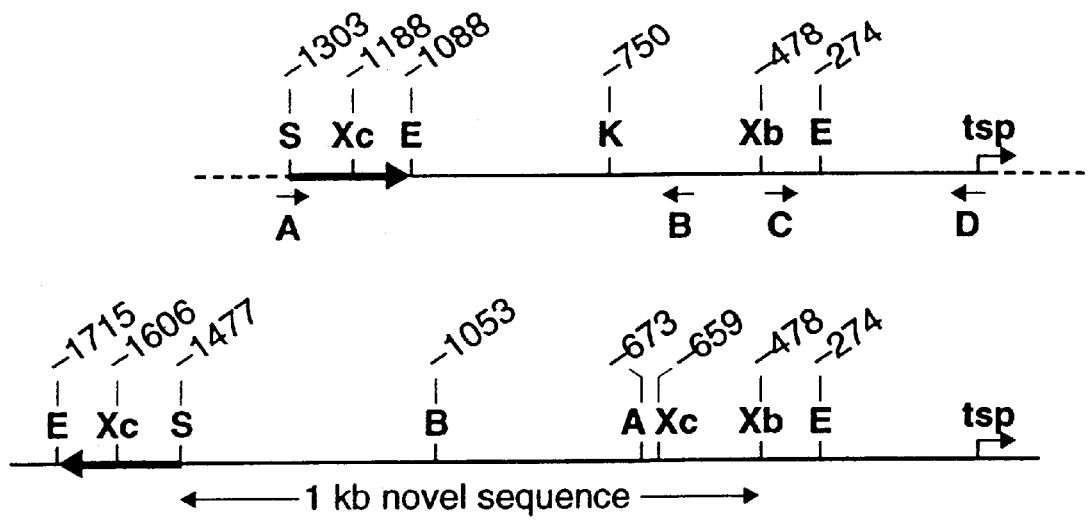
FIGS. 1A–1C shows the results of PCR analysis of cloned stromelysin promoter regions and human DNA samples.

The following definitions are set forth to illustrate and define the meaning and scope of the various terms used to describe the invention herein.

The term "HSL-1" refers to human stromelysin-1, a member of the matrix metalloproteinase (MMP) family that digests a broad spectrum of extracellular matrix components.

The term "promoter region" refers to a region of DNA that functions to control the transcription of one or more genes, and is structurally identified by the presence of a binding site for DNA-dependent RNA polymerase and of other DNA sequences on the same molecule which interact directly or indirectly to regulate promoter function.

The term "transcriptional regulator" refers to a biochemical element that acts to prevent or inhibit the transcription of a promoter-driven DNA sequence under certain enviromental conditions (e.g., a repressor or nuclear inhibitory protein) and to permit or stimulate the transcription of the promoter-driven DNA sequence under other environmental conditions (e.g., an inducer or enhancer).

The term "induction" refers to an increase in gene expression brought about by a transcriptional inducer, relative to some basal level of expression.

The term "repression" refers to a decrease in gene expression brought about by a transcriptional repressor.

The term "enhancer" refers to a DNA sequence that interacts directly or indirectly with a gene promoter on the same DNA molecule to increase its activity.

The term "transformed" or "transfected" refers to the process by which exogenous DNA is transferred into an appropriate host cell.

The term "vector" refers to any carrier of exogenous DNA that is useful for transferring the DNA to a host cell for replication and/or appropriate expression of the exogenous DNA by the host cell.

The term "operably-linked" refers to the positioning and covalent linkage of a heterologous DNA sequence within a recombinant DNA vector such that its expression can be driven by a regulatable promoter contiguous therewith.

The term "treatment" or "treating" means any treatment of a diseases in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

Procedure Parameters

Unless specified to the contrary, standard techniques and parameters are used in the present invention. The procedures described herein employ aqueous media, solutions and buffers, and take place at atmospheric pressure within a temperature range from $-70°$ C. to $100°$ C. (preferably from $10°$ C. to $35°$ C.; most preferably at "room" or "ambient" temperature (e.g., $20°$ C.). Further, unless otherwise specified, the reaction times and conditions are intended to be approximate, e.g., taking place at about atmospheric pressure within a temperature range of about $-70°$ C. to about $100°$ C. (preferably from about $10°$ C. to about $35°$ C.; most preferably about $20°$ C.) over a period of about 1 to about 10 hours (preferably about 5 hours). Parameters given in the Examples are intended to be specific, not approximate.

Isolation and purification of the biomolecules described herein can be effected by procedures specifically illustrated or referred to in the examples hereinbelow. However, other equivalent separation or isolation procedures can, of course, also be used.

Isolation, Characterization and Function of the HS-1 Promoter

As noted above, the present invention relates to an isolated HSL-1 promoter region whose structural and functional properties tested thus far are identical to those of the native genomic HSL-1 promoter. A partial sequence of the isolated HSL-1 promoter region is disclosed in SEQ ID NO: 1. This sequence can be employed by those skilled in the art, using accepted methodology, to practice the invention as described without undue experimentation. For example, see Sambrook, Fritsch and Maniatis, *Molecular Cloning: a laboratory manual*, Second Edition (Cold Spring Harbor Laboratory Press, New York) 1989.

Figure 4:
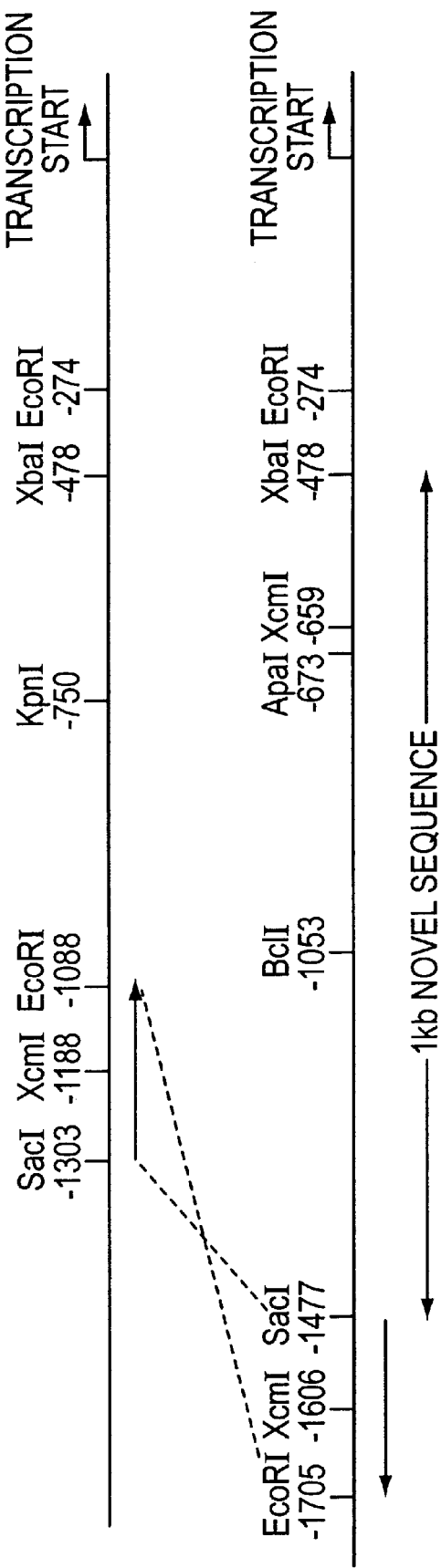
FIG. 4 is a comparison of the restriction map of the published stromelysin promoter (upper map) from the −1303 SacI site to the transcription start site with the map of the pSKStrB stromelysin promoter (lower map) from the −1705 EcoRI site to the transcription start site. A double-headed arrow is drawn below the 1.0 kb sequence that is absent from the published clone. Dashed lines show the portion of the published clone that exists in pSKStrB in inverse orientation (underlined with heavy arrows).

Alternatively, those skilled in the art can practice the invention by repeating the experimental procedures carried out by the present inventors for the isolation, characterization and functional assays of the HSL-1 promoter in a host cell system. As described in greater detail in the Examples and Figures, genomic clones that encoded stromelysin-1 were isolated by screening human genomic DNA libraries (Example 1). A 4 kb fragment encompassing the promoter region plus the first three exons of the stromelysin-1 gene was subcloned into a plasmid vector, and the resulting construct was used to transform *E. coli* (Example 2). The cloned promoter of the invention (designated pSKStrB) differed substantially from an HSL-1 promoter (designated −1303+4HGH) that was cloned by other workers and stated to accurately reflect the native genomic promoter, as revealed by Southern blots of PCR-amplified fragments and EcoRI-digestion products (Example 3, FIGS. 1 and 2). The promoter region of pSKStrB was partially-sequenced (Example 2, FIG. 3 (SEQ ID NO:1)). A restriction map of the sequenced portion of the promoter was obtained (FIG. 4). PCR amplification using pSKStrB, human genomic DNA samples and an independently cloned promoter (designated 682) as templates and a primer set designed on the basis of SEQ ID NO:1 gave the expected product size (i.e. 0.43 kb)(Example 3, FIG. 5). EcoRI-digestion of both cloned promoters and human genomic DNA samples gave a predicted 1.4 kb fragment (Example 3, FIG. 6). Promoter regions of various lengths up to 1515 bp were subcloned into reporter gene vectors (Example 4, FIG. 7). The functionality of the subcloned promoter regions was demonstrated in transient transfection assays performed in cells stimulated with known inducers of HSL-1 (e.g., IL-1β+TNF-α, PMA) (Example 5, FIG. 8).

Characterization of the promoter regions of pSKStrB and 682

The promoter region of pSKStrB is identified by the partial sequence shown in FIG. 3 (SEQ ID NO: 1). The sequence from −480 to −1480 is novel. The region between −480 and the transcription start site appears to be identical to the corresponding sequence of the previously published clone (−1303+4).

The promoter regions of pSKStrB and 682 differ from that of the published clone in the ordering of the SacI-EcoRI segment upstream of the novel 1 kb sequence, which is inverted relative to the corresponding sequence of clone 1303+4HGH (FIG. 4).

Functionality of the pSKStrB Promoter Region

A 1.5 kb reporter gene construct of the pSKStr promoter region (−1515+40StromZ) was determined to be functional in eucaryotic cells. When transferred to a eukaryotic cell line that normally produces stromelysin mRNA, this construct, which contains sequences not previously reported, was able to direct the synthesis of β-galactosidase when the cells were stimulated with the cytokines IL-1β and TNF-α, or with the tumor promoter PMA (Example 5, FIG. 8). The levels of induction obtained with −1515+40StromZ were comparable to those obtained with −280+40StromZ.

Based on the foregoing characterization and demonstration of functionality of the cloned promoter of this invention, this invention can be used in research and therapeutic applications requiring a native promoter architecture for tissue-specific transcription of HSL-1. In particular, this invention is useful in screening for pharmacologic agents that modulate HSL-1 levels either by affecting signal transduction pathways that necessarily precede transcription or by directly affecting the transcription of the HSL-1 gene.

For screening purposes, appropriate host cells are transformed with a vector having a reporter gene under the control of the cloned HSL-1 promoter of this invention. The transformed host cells are induced with proinflammatory cytokines such as IL-1 and TNF-α, or with a phorbol-type tumor promoter, in the presence or absence of a pharmacologic agent with known activity (i.e a standard agent) or putative activity (i.e. a test agent) and the expression of the reporter gene is measured. A change in the level of expression of the reporter gene in the presence of the test agent is compared with that effected by the standard agent. In this way, active pharmacologic agents are identified and their relative potency in this assay determined.

Host cells that respond to proinflammatory cytokines that induce stromelysin-1 promoter activity in this assay include: SW1353 (ATCC HTB94), a human chondrosarcoma line; and U-2 OS (ATCC HTB96), a human osteogenic sarcoma line. It is intended that the assay not be limited to these specific cell lines, insofar as any host cells with the requisite characteristics can be used in the assay.

This invention is also useful for gene therapy of disease states involving overexpression of MMPs.

For gene therapy applications, vectors are used that are capable of expressing heterologous genes other than β-galactosidase and luciferase in a eukaryotic cell. These vectors contain one or more heterologous genes whose expression is desired, e.g., genes encoding tumor necrosis factor receptors and tissue inhibitors of matrix metalloproteinases, at least one eukaryotic selectable marker gene, a human stromelysin-1 promoter sequence of the present invention positioned so as to promote transcription of the heterologous gene or genes or interest, the appropriate eukaryotic transcriptional start and translational stop signals, at least one Shine-Dalgarno sequence and initiator codon, a sequence that signals polyadenylation of the transcript MRNA, and any other DNA sequences necessary or preferred for appropriate transcription and subsequent translation of the vector DNA. These additional sequences may include a signal sequence for proteins to be exported or secreted from the host cell and at least one gene for a transcriptional regulator protein. In addition, when the vector is to be used as an extrachromosomal replicating DNA in the eukaryotic cell where it is expressed, the vector will include an origin of replication that functions in the host cell.

When used as a shuttle vector, the vector will contain a second origin of replication that functions in another host cell, e.g. *E. Coli*, and a second selectable marker gene for use with the alternative host cell. When the vector is to be integrated into the host chromosomal DNA, it will contain elements necessary to facilitate its integration into the host genome. These elements may be provided by viral vectors, such as vaccinia or adenovirus, or by non-viral recombinant plasmids.

Any additional features that may be required may be added to these vectors using methods known to those of ordinary skill in the art, in light of the teachings herein.

DNA is commonly transferred into recipient mammalian cells by calcium phosphate-mediated gene transfer gene transfer, electroporation, or viral infection. General methods, vectors, and general considerations for gene transfer and expression may be found in M. Kriegler, *Gene Transfer and Expression: A Laboratory Manual*, Stockton Press, 1990. Direct gene transfer to cells in vivo is achieved by the use of modified viral vectors, including retroviruses, adenoviruses, adeno-associated viruses and herpes viruses, liposomes, and direct injection of DNA into certain cell types. In this manner, recombinant genes can be delivered into specific target tissues in vivo. See, e.g, Wilson, Nature, 365: 691–692 (1993); Plautz et al, Annals NY Acad. Sci. 716: 144–153 (1994); Farhood et al, Annals NY Acad. Sci. 716: 23–34 (1994); and Hyde et al, Nature 362: 250–255 (1993). As well, cells transformed with recombinant DNA ex vivo may be introduced at localized sites of inflammation by injection, e.g. intra-articular, intracutaneous, intramuscular and the like.

EXAMPLES

The following examples are given to enable those skilled in the art to more clearly understand and to practice the present invention. They should not be considered as limiting the scope of the invention, but merely as being illustrative and representative thereof.

Example 1

Cloning of the Human Stromelysin-1 Promoter

1A. The genomic clone from which clone pSKStrB was derived was isolated by screening a human genomic DNA library made from placenta and cloned into bacteriophage lambda (λ-fixII; Stratagene, La Jolla, Calif.) with a 714-bp SacI-HindIII fragment of a stromelysin-1 cDNA clone. Positively hybridizing phage were subjected to a secondary screen with an oligonucleotide that distinguishes between stromelysin-1 and -2. The sequence of this oligonucleotide is: 5' ctcactgcccttaccttc 3' SEQ ID NO:2. A phage clone hybridizing to stromelysin-1 cDNA but not to the stromelysin-2 oligonucleotide was isolated. DNA was prepared from this phage, digested with BamHI and subcloned as described in Example 2.

1B. Clone 682 was isolated from a bacteriophage P1 library according to the method of Smoller et al., Chromosoma 100: 487–494 (1991), which is herein incorporated by reference . The bacteriophage, carrying 60 to 80 kb inserts of human DNA cloned into the BamHI-cut vector pAD10SacBII, were used to infect *E. coli* cells. Bacterial clones were screened for their ability to give a circa 100 bp PCR product using the following primers from sequences within exon 3 of the stromelysin-1 gene: 5' gccaaaagatgctgttgattc 3' SEQ ID NO:3 and 5' cagcctctccttcatacagc 3 SEQ ID NO:4. Clone 682 DNA was purified from a single bacterial clone showing the expected size PCR product.

Example 2

Subcloning and Sequencing of the NSL-1 Promoter Region

A 4.0 kb BamHI fragment of the human genomic DNA clone from Example 1A encompassing the promoter region plus the first three exons of the stromelysin gene was subcloned into pSK (Stratagene, La Jolla, Calif.) by standard molecular biology techniques described in F. M. Ausubel et al, eds., *Current Protocols in Molecular Biology*, John Wiley and Sons, 1994, herein incorporated by reference. The recombinant plasmid is designated pSKStrB.

The clone pSKStrB and subcloned fragments thereof were sequenced up to −1706 of the promoter. DNA sequencing was performed with an Applied Biosystems (ABI) DNA Sequencer Model 373A using the dideoxy chain termination method. Sequence analysis of the promoter region confirmed the presence of stromelysin-1 and not stromelysin-2.

Example 3

3A. PCR Analysis of Cloned Promoter Regions and Human DNA Samples

PCR was performed on 100 ng DNA in 20 $\mu$l reaction volumes consisting of 200 $\mu$M dNTPs, 10 mM TrisHCl (pH 8.3), 50 mM KCl, 1.5 mM $MgCl_2$, 0.5 $\mu$M each primer, and 1 u Taq DNA polymerase (Boehringer-Mannheim), at 94° C. for 90 s, 55° C. for 90 s(for plasmid controls) or 42° C. (for human DNAs) and 72° C. for 2 min., for 25 cycles. PCR products were electrophoresed through 1.2% agarose gels in 1×TBE and analyzed by Southern blotting (described in Example 3B). Based on the published sequence of the cloned HSL-1 promoter, the following primers were used for the PCR analysis shown in FIG. 1:

Primer A: 5' tcagaagcttgagctctgggatcaagtg 3' SEQ ID NO:5;
Primer B: 5' cagataccatgctaagtacta 3' SEQ ID NO:6;
Primer C: 5' tagtatagactatagctgta 3' SEQ ID NO:7; and
Primer D: 5' cctcgggagcgcagcttta 3' SEQ ID NO:8.

Figure 5A:
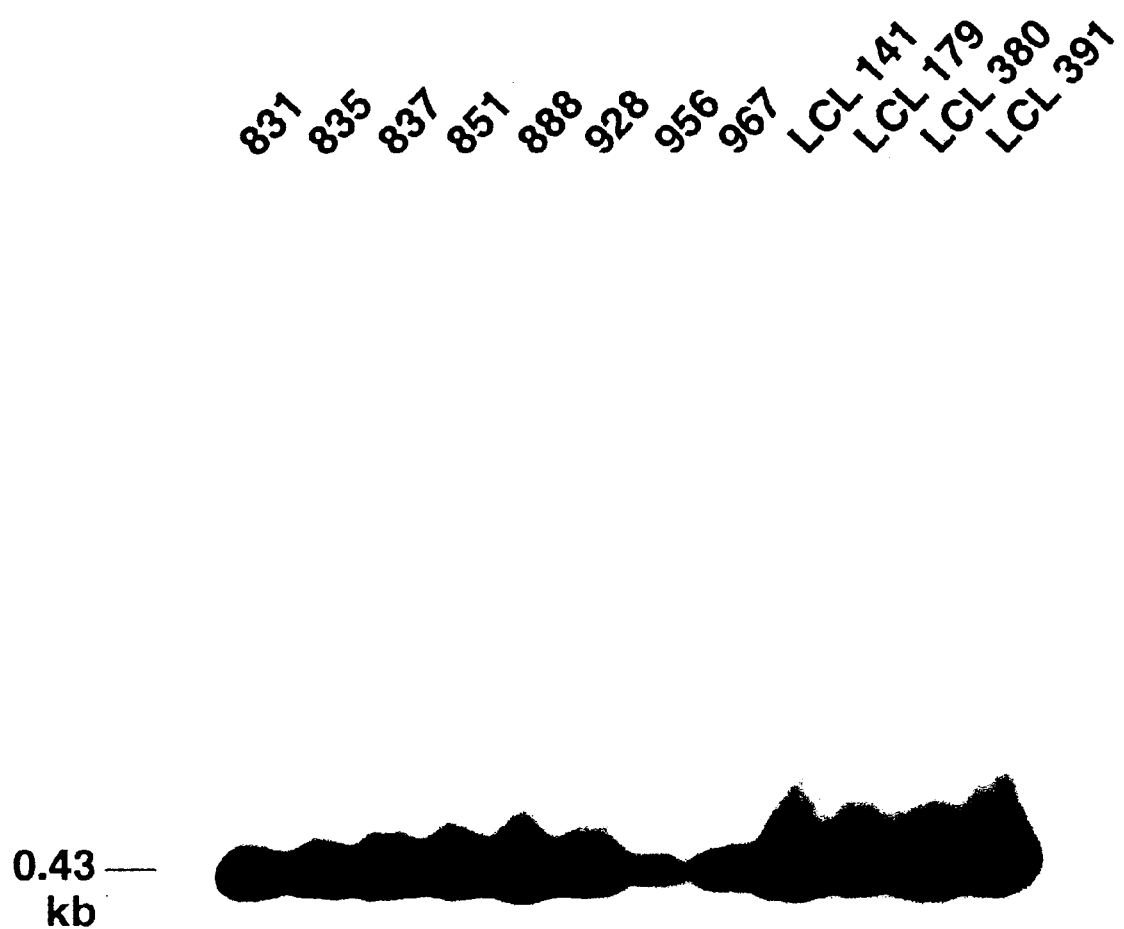
FIGS. 5A–5B shows the results of PCR analysis of human DNA samples (FIG. 5A) and cloned stromelysin promoter regions (FIG. 5B) as templates, using as the forward primer the region of the novel 1.0 kb sequence from −744 to −768 and as the reverse primer the sequence −339 to −360 (See FIGS. 3A–3C). The Southern blots shown here were probed as described for FIGS. 1A–1C. The position of the expected 0.43kb product is indicated on the sides of FIGS. 5A–5B. Sample 15ST5Z is a clone consisting of the −1515 to +40 region in a reporter gene vector.
Figure 5B:
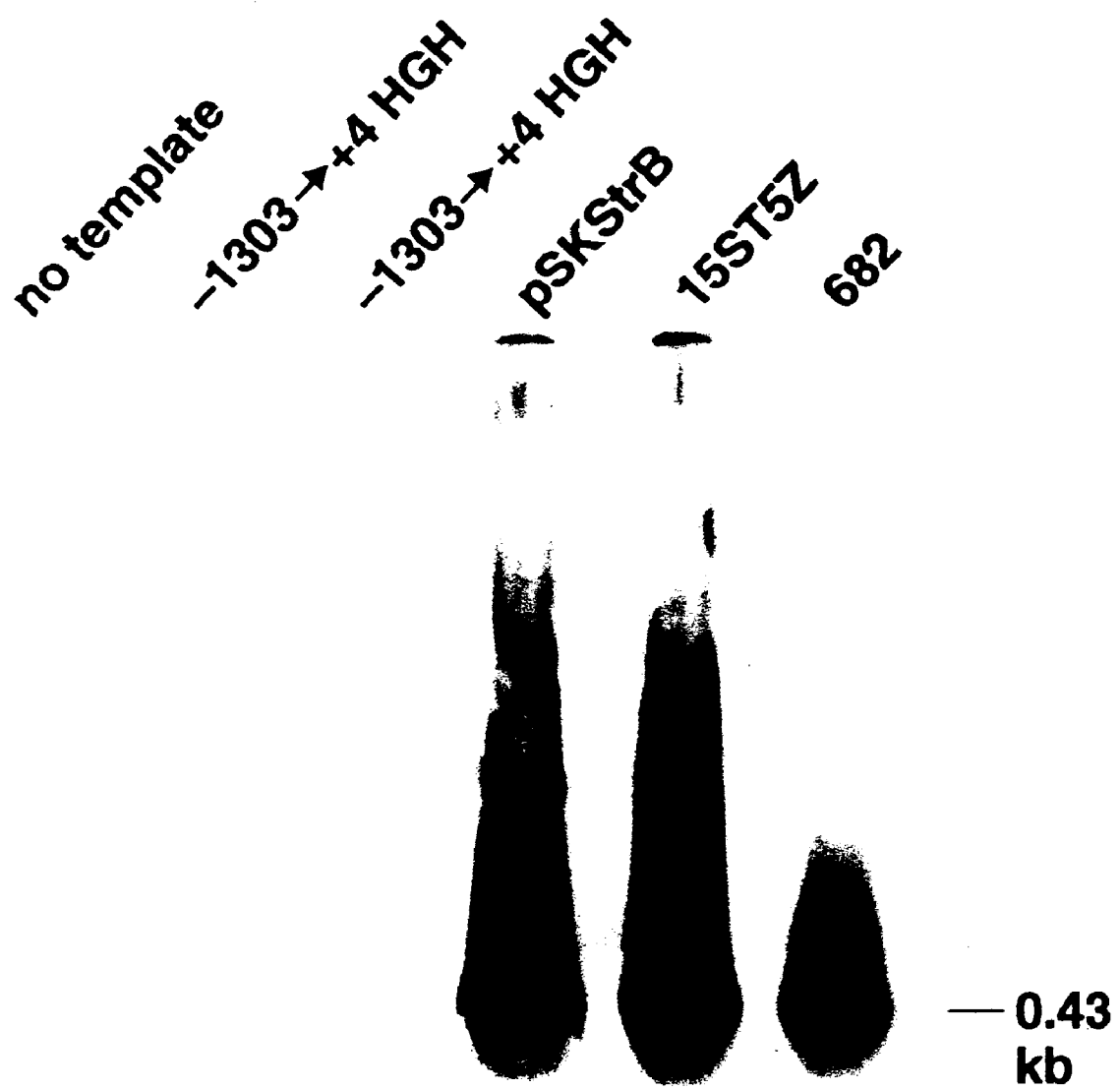

Based on the SEQ ID NO:1 of the present invention, the following primers were used for the PCR analysis shown in FIG. 5:

5' catgtgtagaagacaaggacagaga 3' SEQ ID NO:9; and
5' ctgcttttagaagttctgcaca 3' SEQ ID NO:10.

3B. Southern Blot Analysis of PCR Products and EcoRI Digests

Agarose gel-fractionated PCR products and EcoRI digestion products of cloned HSL-1 promoter regions and human genomic DNA samples were blotted onto Nytran membranes (Schleicher and Schuell, Keene, N.H.) in 10×SSPE, and the DNA was UV-crosslinked to the membrane using a Stratalinker (Stratagene, La Jolla, Calif.). Blots of cloned promoter DNA were hybridized in 2×SSPE, 0.1% SDS at 65° C., and washed in 0.1×SSPE, 0.1% SDS at 68° C. Human genomic bNA blots were pre-hybridized and hybridized in a solution of 50% formamide, 5×SSPE, 2×Denhardt's solution, 0.2% SDS, 200 $\mu$g/ml salmon sperm DNA and 9% dextran sulfate, at 42° C., and washed in 0.1×SSPE, 0.1% SDS at 55° C. The blots shown in FIGS. 1, 2 and 5 were probed with a HindIII-BamHI fragment containing −1303 to +4 of the published HSL-1 promoter clone. The blot shown in FIG. 6 was probed with the SacI-XbaI fragment (−1480 to −480) of pSKStrB). Both probes were labeled using the random-primed method (Feinberg and Vogelstein, Anal. Biochem. 137: 266 (1984), which is herein incorporated by reference.

Figure 1B:
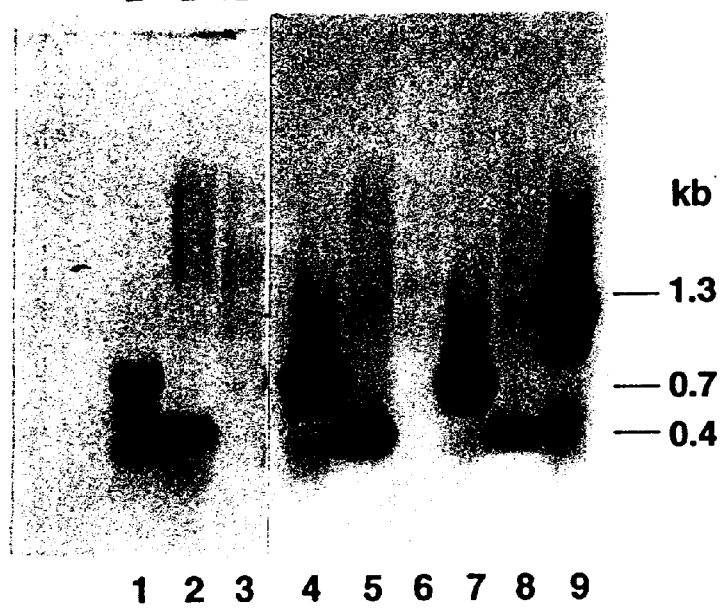
Figure 1C:
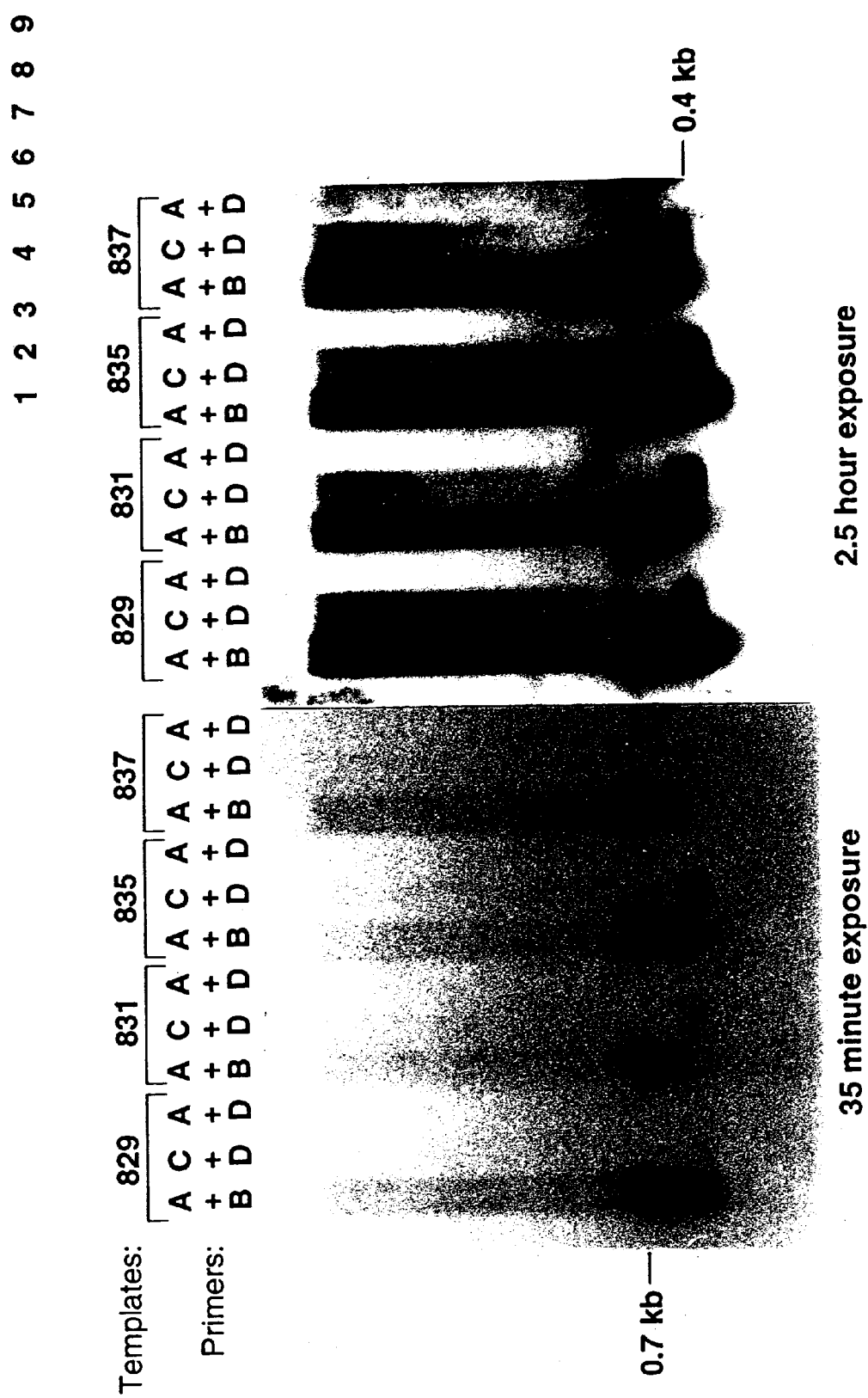

Referring to FIG. 1, this analysis showed that PCR primers A+D designed on the basis of the published sequence of clone −1303+4 did not give the expected 1.3 kb when pSKStrB, 682 or genomic DNA samples were used as templates. This product was seen only with −1303+4HGH. However, as shown in FIG. 5, using oligonucleotide primers that flank the −480 XbaI site (from −768 to −744 and from −339 to −360), pSKStrB, 682 and genomic DNA templates all showed an expected 0.43 fragment on Southern blots probed with the −1480 to −480 novel sequence. No product is seen with the −1303+4HGH template, however.

Figures 2A, 2B:
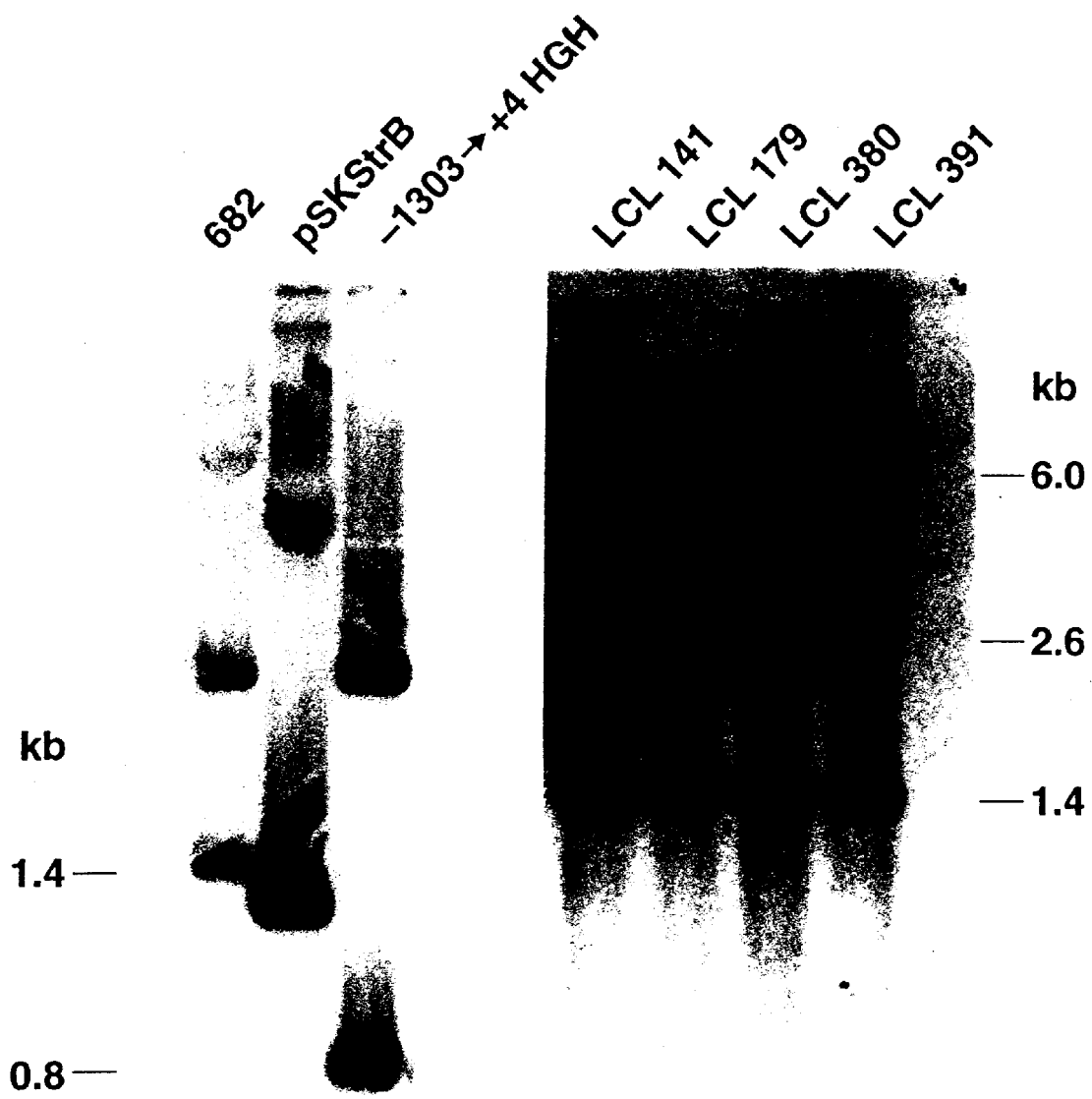
FIGS. 2A–2B shows EcoRI digests of human genomic DNA samples and cloned stromelysin promoters. Southern blots were probed as described in FIG. 1A–1C. Sizes of fragments generated from within the plasmid insert are shown in FIG. 2A, left side. Additional bands in pSKStrB are from hybridization to an EcoRI fragment between −280 and an EcoRI site in the polylinker and to the remainder of the insert upstream of the 5'-most EcoRI site plus the vector. The additional band in −1303+4HGH is from the remainder of the insert on either side of the EcoRI fragment plus the vector. The additional band in 682 is 2.6 kb .
Figures 6A, 6B:
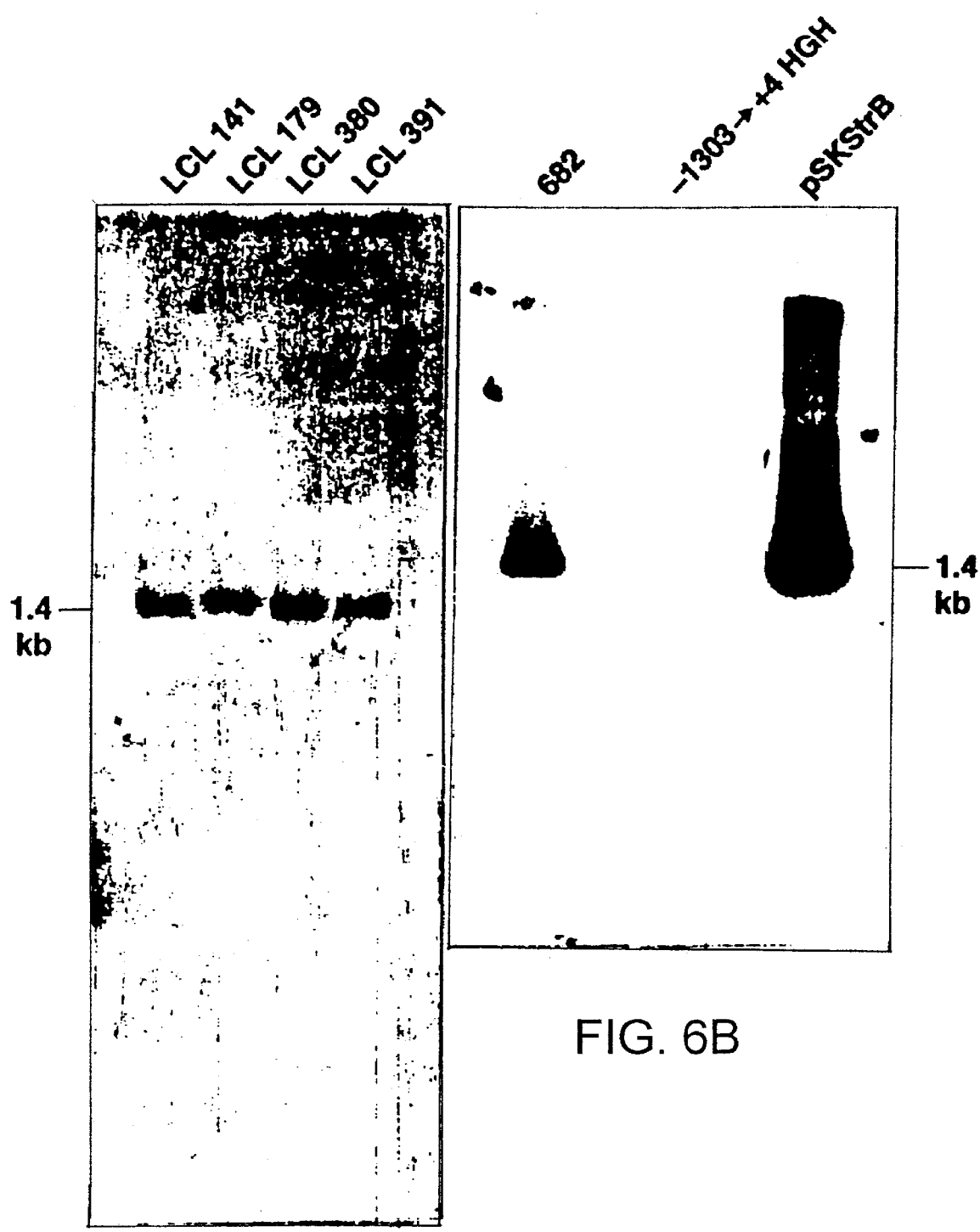
FIGS. 6A–6B shows the results of Southern blots of EcoRI-digested human DNA samples (FIG. 6A) and cloned promoter regions (FIG. 6B) probed with the novel 1.0 kb fragment (−1480 to −480). The fragment was excised from pSKStrB with the restriction enzymes SacI and XbaI and radiolabeled prior to hybridization with the blots. The position of the expected 1.4 kb fragment is indicated on the sides of FIGS. 6A–6B.

Referring to FIG. 1A and FIG. 2, restriction of −1303+4HGH with EcoRI yields an expected 0.8kb product on Southern blots probed with the HindIII-BamHI fragment of −1303+4HGH. This fragment was not seen in clones pSKStrB and 682, or in human genomic DNA samples. Instead, these clones and the human DNAs share a 1.4 kb EcoRI fragment which is absent from −1303+4HGH. This fragment hybridizes with the −1480 to −480 novel segment of pSKStrB. By contrast, no band is detected in an EcoRI digest of clone −1303+4HGH (FIG. 6).

Taken together, these analyses prove that the sequence between the −1480SacI and −480 XbaI site exists in the cloned promoters of this invention and in the human genome but does not exist in the published sequence of clone −1303+4HGH.

Example 4

Stromelysin-1 Promoter Expression Vectors

4A. Stromelysin-1 promoter regions were cloned into the reporter gene vector, pSDKLacZ PA (provided by Dr. Lynn Matrisian, Vanderbilt University), and hereafter referred to as pSDKZ (see FIG. 7), as follows. Oligonucleotides complementary to a 15 to 18 bp region on the 5' and 3' ends of the portion to be cloned were synthesized for use as PCR primers. The 5' oligonucleotide primer contained a HindIII site at its 5' end. A PstI site was included on the 5' end of the 3' oligonucleotide. These PCR primers were then used to prime synthesis of a promoter fragment, using pSKStrB as the template. To facilitate cloning of PCR products, the resulting PCR product was subdloned into the "TA" cloning vector pCRII (Invitrogen Corp., San Diego, Calif.) according to the protocol supplied by the vendor. The promoter fragment was excised from PCRII with HindIII and PstI and ligated to pSDKZ that was digested with both HindIII and PstI. In this manner, the reporter gene constructs −280+40Strom-Z, −1643+40Strom-Z and −1515+40Strom-Z were made in PSDKZ. These constructs express β-galactosidase under the control of the stromelysin-1 promoter.

A second reporter gene vector, pGL2-Basic (Promega Corp.,Madison, Wis.) was used to make constructs with firefly luciferase as the stromelysin-1 promoter-driven gene. Promoter fragments were subcloned into this vector as described above, except for the use of different restriction enzymes for subcloning the fragments from pCRII as mandated by the available pGL2-Basic polylinker restriction enzyme sites. 4B. Similarly, by performing the procedure of part A and substituting a reporter gene in the vector with a gene encoding tumor necrosis factor receptor; and a gene encoding tissue inhibitor of matrix-metalloproteinase; there is obtained: an expression vector containing a stromelysin-1 promoter-driven gene for tumor necrosis factor receptor; and an expression vector containing a stromelysin-1 promoter-driven gene for tissue inhibitor of matrix metalloproteinases.

Example 5

Cloned HSL-1 Promoter Function

5A. Cell Lines

The ability of the cloned promoter to direct the synthesis of a heterologous gene in eukaryotic host cells was tested using the human cell lines SW1353 (ATCC HTB 94) and U–2 OS (ATCC HTB 96). Cells were cultured in standard growth medium containing 10% fetal bovine serum and penicillin-streptomycin at 37° C. in a tissue culture incubator.

5B. Transfection

Figure 7A:
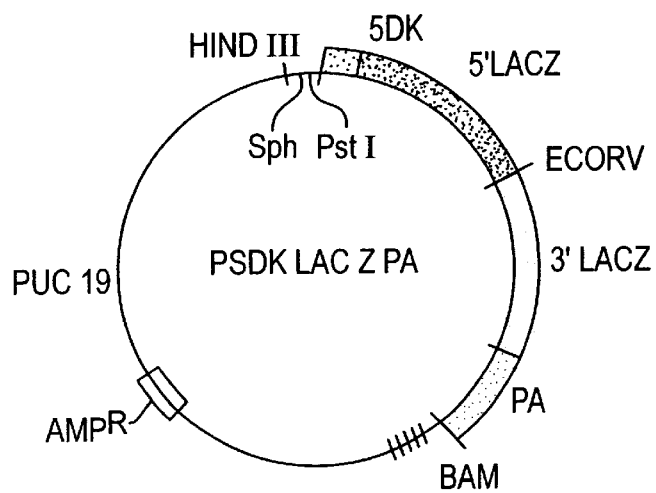
FIGS. 7A–7B illustrates the reporter gene vectors that were used for constructing expression systems containing regions of the human stromelysin-1 promoter of this invention.
Figure 7B:
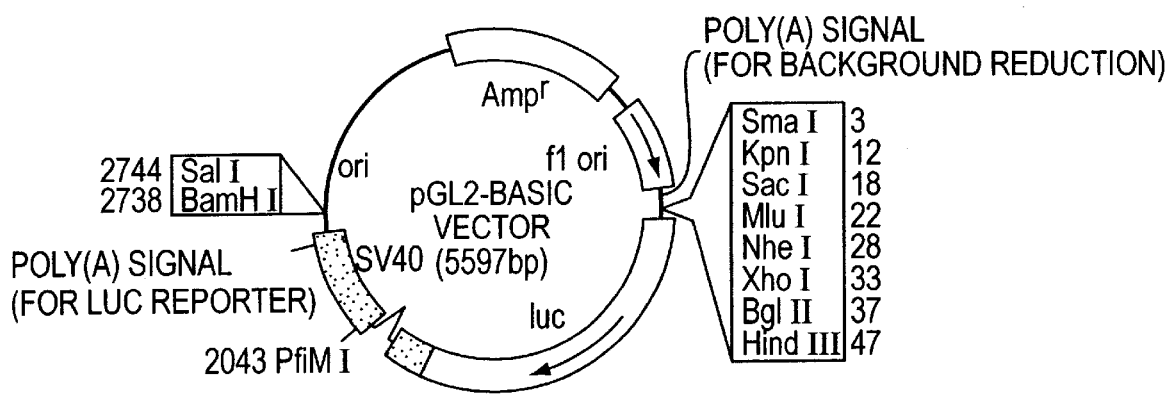

Cells were transiently transfected with reporter gene constructs utilizing the pSDKZ and pGL2-Basic vectors (see FIG. 7 for detailed maps). SW1353 cells were transfected using the calcium phosphate precipitation method, and U–2 OS were transfected by electroporation.

5C. Assay Conditions

The description below pertains to promoter constructs in pSDKZ, although similar results were obtained with pGL2-Basic.

The following constructs were tested for activity: –200+40Strom-Z, 200-AP$^1$+40Strom-Z, (deleted in AP$^1$); –280+40Strom-Z; and –1515+40Strom-Z. Inducibility of the cloned promoter regions was tested by adding IL-1β plus TNFα at 10 ng/ml and 50 ng/ml, respectively, or PMA at 100 nM final concentration to the culture medium in 96-well tissue culture plates. Approximately 18 hours later, the cells were assayed for lacZ expression using the MUG (4-methylumbelliferyl-β-D-galactoside) assay essentially as described in Roederer et al, *Methods: A Companion to Methods in Enzymology* 2: 248–260 (1991). Specifically, this entailed lysing the cells and adding the substrate 4-methylumbelliferyl-β-D-galactoside which, when acted upon by β-galactosidase, yields a strongly fluorescent product, 4-methylumbelliferone. The presence of the fluorescent product was measured using a Fluoroskan. Values were normalized for transfection efficiency by co-transfection with the plasmid SEAP (a plasmid that has the gene encoding Secreted Alkaline Phosphatase under the control of the constitutive RSV (Rous sarcoma virus) promoter), and measuring the amount of alkaline phosphatase produced using a fluorimetric assay.

Figure 8:
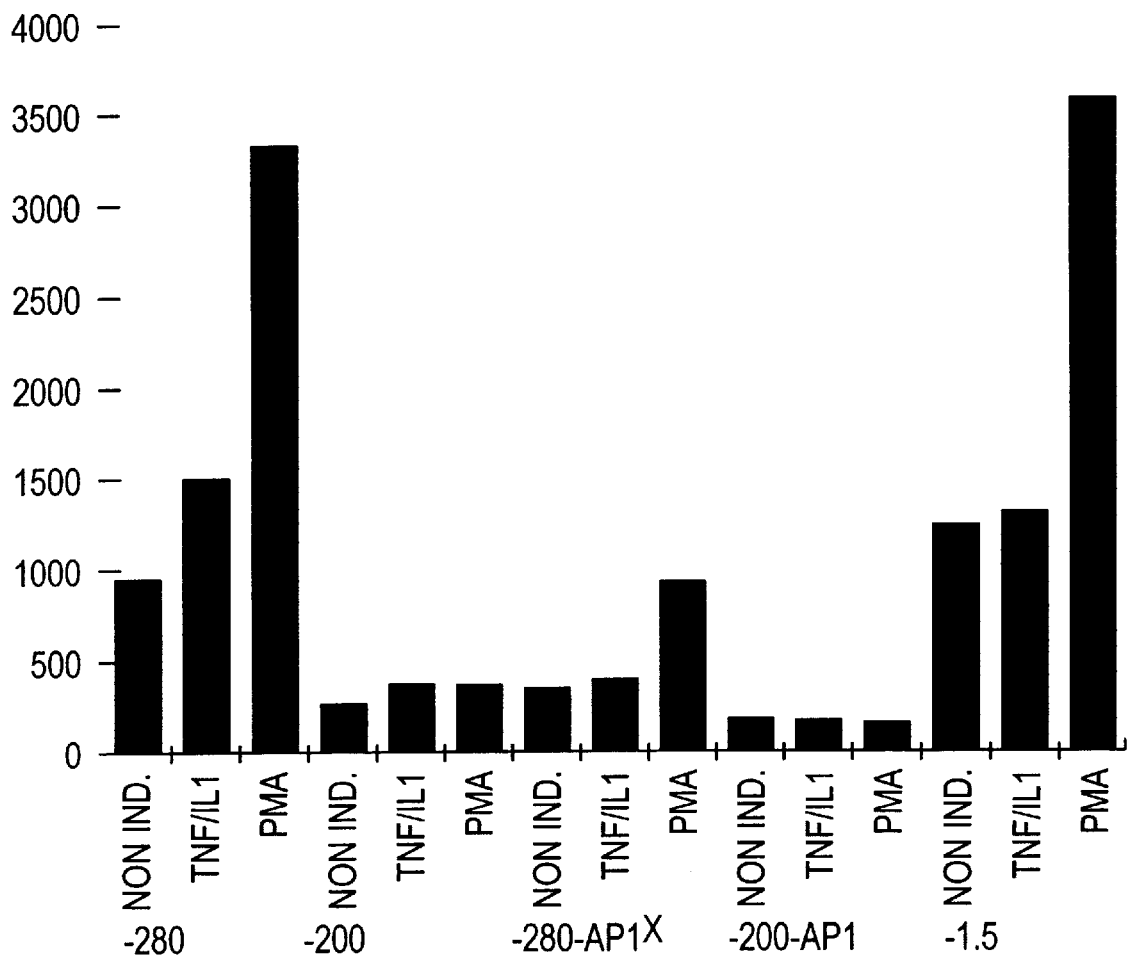
FIG. 8 graphically depicts results of a representative transient expression assay carried out in SW1353 human chondrosarcoma cells with various lengths of stromelysin-1 promoter cloned into the PSDKZ vector of FIG. 7A. The heights of the bars represent fluorescence (arbitrary units) produced by β-galactosidase-catalyzed hydrolysis of 4-methyumbelliferyl-β-D-galactoside, normalized to background. Values are normalized for transfection efficiency. Under the conditions of the assay, fluorescence is proportional to lac Z expression. The identity of the corresponding inducer tested, if any, is shown beneath each bar. The promoter fragment lengths tested for each assay group is also shown. Abbreviations: TNF/IL1: tumor necrosis factor-α+ interleukin 1β; PMA: phorbol myristyl acetate; Non Ind.: inducer not added to assay medium. The following abbreviations specify regions of the stromelysin-1 promoter (relative to the transcription start codon) driving lacZ expression: −280, −200; −1.5 (i.e., −1500 bp), −280-AP1$^x$ (i.e. −280 lacking AP1 site) ; and −200-AP1 (i.e. −200 lacking AP1 site).

Representative assay results are shown in FIG. 8. These results demonstrate that the clone –1515+40Strom-Z consisting of the HSL-1 promoter region from –1515 to +40 driving lacZ expression and containing sequences not previously reported, directed the synthesis of β-galactosidase when present in a eukaryotic cell line that normally produces stromelysin mRNA, when the cells were stimulated with the cytokines IL-1β and TNFα, or with the tumor promoter PMA. Further, the level of stimulation with this construct was comparable to that obtained with the –280+40Strom-Z construct.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed:

1. A method for measuring stromelysin-1 promoter activity comprising:
   (a) contacting a host cell with a proinflammatory cytokine or a tumor promoter, wherein said host cell is transformed with an expression vector comprising a heterologous gene encoding a cytokine receptor or an endogenous inhibitor of matrix metalloproteinases, said gene operably linked to a promoter comprising a sequence selected from the group consisting of
      (i) SEQ ID NO:1 or a fragment thereof exhibiting promoter activity that can be induced by proinflammatory cytokines or tumor promoters, wherein said fragment is at least 1.47 kb; and
      (ii) the fully complementary strand of (i): and
   (b) measuring the activity of stromelysin-1 promoter by detecting the presence of the heterologous gene product.

2. The method of claim 1 further comprising:
   (c) adding a putative activator or inhibitor of stromelysin-1 promoter activity; and
   (d) measuring the activity of stromelysin-1 promoter by measuring the expression of said heterologous gene product.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1772 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GAATTCACAT CACTGCCACC ACTCTGTTCT CCTTGTCCTC ATATCAATGT GGCCAAATAT     60

TTTCCCTGTA TTTCAATCAG GACAAGACAT GGTTTTTTCC CCCCATCAAA GGAATGGAGA    120

ACCATAGAAT ACTAGTTTTA AAATGTCTTT AGGCCAGGTG CCGTGACCCA TGTCTGTAAT    180

CCTAGCACTT TGAGAGGTTG AGGCAGGAGA ATCACTTGAT CCCAGAGCTC GAAACCAGCC    240

TGGGCAACAT AGTGAAACCT CTGTCCCTAT TTTTTAAATA AAACTTGAAA AAGTCTTTAG    300

ACATAATCTA GTCTATAAAT GAAGGCTTAA ATGTGATGTA TAGCCCCCTG CCAAGTGGCT    360

ATCACCTGTG TGGGCATCTT CAGTCATAGG GATCTTATTG CCACAGAGAA ATCCCTTTAA    420
```

-continued

```
ACTTATTGGG TAAAATCTCT CCAATGTTTA TTAAGAAACA CACAAAAAAT AAAGCAAAGA      480

AGAAAATGCA AAAGAGTTAT AAATGAGAGG AAGCAAAATG GGCACTTATT AAAGGTCTAA      540

TAAATGCACA TTTGTATCCA TCATTCTACT GAGTTCTTAC TCCCAAGATG TTCTTCCCTT      600

TAGCAAACAA ATAAGCAAGT CAGCAAAGAA AGAAAGAACA AACAAAATGT GGTGATCAGG      660

GAAGCATTGA GGAGATGGAT GGTGGCAGGT GGCAAGAGGA CTATAAAAGT TTTACAAAAT      720

GTCTTCCTCT GAATATGTTT AGAGTCTTGC ATTCAAGCAT TTATTATACA ACCAATAATG      780

TGAGCAACAC TTTACTTGAC AAAGAAACAG AAAAGAAAGG AAAGGAAGAA AACAGAAGAG      840

CATGAAGAGA AAATTTAGGA TGGATTCTGT TCTTCAACTT CAAAGCATCT GCTAATTTGA      900

ATTTAGGGAG GAGGGGAAAA GGTTGAAAGA GAATAAGACA TGTGTAGAAG ACAAGGACAG      960

AGAGAATTTC AGTCCGGTAA GCAATGTAAT TCATTTCAGT TCTACAACTA TTTATGGAGC     1020

AGCTACGTGG GCCCATCACC CATTAATAAA TTGGTTACAG AATTAAAACC AACCCAAAGG     1080

GAATATACTT CCTTCTTTTT CACAGACCCT CTTTGTTCTA TTCTGCCCAT GAGGTTTTCC     1140

TCCTCAAGAA CCAGCAAATC CAACAGCAGT CAATAGCAGG CATTACAAAT CAGATTCAGA     1200

GAAATAAATC ACCCCTTCTA AATTTCTTCT AGATATTATC TTTTATGTTT TGAGTATAAT     1260

TGTATATAGT ATAGACTATA GCTATGTATG TACACTTTCC ACTTACATCT TTTATTTGCT     1320

TTTATAATGT CTTTCTTAAA ATAAAACTGC TTTTAGAAGT TCTGCACAAT TCTGATTTTT     1380

ACCAAGTCAA CCTACTTCTT CTCTCAAAAG GACAAACATA AATTGTCTAG TGAATTCCAG     1440

TCAATTTTTC CAGAAGAAAA AAAATGCTCC AGTTTTCTCC TCTACCAAGA CAGGAAGCAC     1500

TTCCTGGAGA TTAATCACTG TGTTGCCTTG CAAAATTGGG AAGGTTGAGA GAAATTAGTA     1560

AAGTAGGTTG TATCATCCTA CTTTGAATTT GGAATGTTTG GAAATGGTCC TGCTGCCATT     1620

TGGATGAAAG CAAGGATGAG TCAAGCTGCG GGTGATCCAA ACAAACACTG TCACTCTTTA     1680

AAAGCTGCGC TCCCGAGGTT GGACCTACAA GGAGGCAGGC AAGACAGCAA GGCATAGAGA     1740

CAACATAGAG CTAAGTAAAG CCAGTGGAAA TG                                   1772

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CTCACTGCCC TTACCTTC                                                     18

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:
```

GCCAAAAGAT GCTGTTGATT C                                                         21

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

CAGCCTCTCC TTCATACAGC                                                           20

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

TCAGAAGCTT GAGCTCTGGG ATCAAGTG                                                  28

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

CAGATACCAT GCTAAGTACT A                                                         21

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

TAGTATAGAC TATAGCTATG TA                                                        22

-continued (2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CCTCGGGAGC GCAGCTTTTA        20

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

CATGTGTAGA AGACAAGGAC AGAGA        25

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

CTGCTTTTAG AAGTTCTGCA CA        22